US011014942B2

(12) United States Patent
Mazzon et al.

(10) Patent No.: US 11,014,942 B2
(45) Date of Patent: May 25, 2021

(54) PREPARATION OF A SOLID FORM OF GADOBENATE DIMEGLUMINE

(71) Applicant: BRACCO IMAGING S.P.A., Milan (IT)

(72) Inventors: Roberta Mazzon, Volpiano (IT); Roberta Fretta, Collegno (IT); Pier Lucio Anelli, Milan (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 16/678,082

(22) Filed: Nov. 8, 2019

(65) Prior Publication Data

US 2020/0071341 A1 Mar. 5, 2020

Related U.S. Application Data

(63) Continuation of application No. 15/321,176, filed as application No. PCT/EP2015/066512 on Jul. 20, 2015, now Pat. No. 10,519,171.

(30) Foreign Application Priority Data

Jul. 24, 2014 (EP) ..................................... 14178283

(51) Int. Cl.
| | | |
|---|---|---|
| *C07F 5/00* | (2006.01) | |
| *A61K 9/14* | (2006.01) | |
| *A61K 9/00* | (2006.01) | |
| *C07C 227/40* | (2006.01) | |
| *A61K 49/10* | (2006.01) | |
| *A61K 49/18* | (2006.01) | |

(52) U.S. Cl.
CPC ............ *C07F 5/003* (2013.01); *A61K 9/0019* (2013.01); *A61K 9/14* (2013.01); *A61K 49/101* (2013.01); *A61K 49/1818* (2013.01); *C07C 227/40* (2013.01); *A61K 49/103* (2013.01)

(58) Field of Classification Search
None
See application file for complete search history.

(56) References Cited

U.S. PATENT DOCUMENTS

| | | |
|---|---|---|
| 3,741,273 A | 6/1973 | Meade |
| 4,916,246 A | 4/1990 | Felder et al. |
| 6,162,947 A | 12/2000 | Ausonio et al. |
| 9,567,350 B2 | 2/2017 | Maisano et al. |
| 9,795,695 B2 | 10/2017 | Anelli et al. |

FOREIGN PATENT DOCUMENTS

| | | |
|---|---|---|
| CN | 1210252 C | 7/2005 |
| CN | 102408348 A | 4/2012 |
| CN | 102712574 A | 10/2012 |
| CN | 102724964 A | 10/2012 |
| EP | 0230893 B1 | 6/1990 |
| EP | 2503990 B1 | 6/2013 |
| WO | 2011-061341 A1 | 5/2011 |

OTHER PUBLICATIONS

CRC Handbook of Chemistry and Physic, 82 Edition 2001-2002, Editor in Chief: David R. Lide, pp. 16-43 to 16-47.
The Merck Index, Senior Editor O'Neil, Maryadele J. et al., XIII Edition, 2001, Nr. 4344, p. 767, Merck & Co., Inc., Whitehouse Station, NJ.
Tung, H. et al ., "Crystallization of Organic Compounds: An Industrial Perspective", Chapter 9: Antisolvent Crystallization, pp. 179-205, John Wiley & Sons, 2009.
US National Library of Medicine: http://chem.sis.nlm.nih.gov/ChemIDplus.
European Search Report for European application No. 14178283.9, dated Dec. 1, 2015 [B0676 EP-P].
PCT International Search Report & Written Opinion of the International Searching Authority for PCT/EP2015/066512, dated Oct. 7, 2015 [B0676 WO].
Office Action for Chinese application No. 201580039408.2, dated Dec. 20, 2017 (English translation) [B0676 CN].
Office Action for Chinese application No. 201580039408.2, dated Oct. 22, 2018, with English translation [B0676 CN].
Office Action for Singapore application No. 11201610655W, dated Oct. 23, 2017 [B0676 SG].
Uggeri, F. et al. "Novel Contrast Agents for Magnetic Resonance Imaging," Inorg. Chem. 34:633-642 (1995).

*Primary Examiner* — Michael G. Hartley
*Assistant Examiner* — Melissa J Perreira
(74) *Attorney, Agent, or Firm* — Vivicar Law, PLLC

(57) ABSTRACT

The present invention relates to a process for the preparation of a solid form of the gadobenate dimeglumine compound that comprises obtaining a solution of the said compound in a suitable solvent A wherein the amount by weight of the water optionally present in the solution is at most equal to or lower than the amount by weight of the gadobenate dimeglumine comprised in the solution and adding the obtained solution to an organic solvent B, acting as an appropriate antisolvent and favoring the formation of a solid form of the gadobenate dimeglumine that can be collected by filtration.

20 Claims, No Drawings

PREPARATION OF A SOLID FORM OF GADOBENATE DIMEGLUMINE

CROSS-REFERENCE TO RELATED APPLICATIONS

This application is a continuation of U.S. application Ser. No. 15/321,176, filed Dec. 21, 2016, which is the national stage application of corresponding international application number PCT/EP2015/066512, filed Jul. 20, 2015, which claims priority to and the benefit of European Application Number EP14178283.9, filed Jul. 24, 2014, all of which are hereby incorporated by reference in their entirety.

FIELD OF THE INVENTION

The present invention relates to a process for the preparation of a solid form of the gadobenate dimeglumine. More particularly, the invention relates to a process using appropriate dissolution and precipitation solvents enabling to collect the gadobenate dimeglumine complex salt as a filterable powder which may be employed, for example, for the preparation of injectable contrastographic formulations for use in the diagnostic imaging field.

STATE OF THE ART

Magnetic Resonance Imaging (MRI) is a renowned diagnostic imaging technique increasingly used in clinical diagnostics for growing number of indications. The undisputed success of this technique is determined by the advantages it offers, including a superb temporal and spatial resolution, the outstanding capacity of differentiating soft tissues and its safety, due to its non-invasiveness and the absence of any ionizing radiation, in contrast to, for instance, X-ray, PET and SPECT.

The strong expansion of medical MRI has further benefited from the development of a class of compounds, the MRI contrast agents, that causes a dramatic variation of the water proton relaxation rates in the tissues/organs/fluids wherein they distributes, thereby providing physiological information in addition to an increase of the anatomical resolution commonly obtainable in the uncontrasted MRI images.

Contrast agents for use in the MRI imaging technique typically include a paramagnetic metal ion, more commonly a gadolinium ion, which is complexed with an aminopolycarboxylic chelating ligand, or a suitable derivative thereof.

Suitable examples of paramagnetic complex compounds that are in the current clinical use as MRI contrast agents include, for instance: Gd-DTPA (the gadolinium complex of the diethylenetriaminepentaacetic acid, N-methylglucamine salt, marketed as Magnevist®), Gd-DOTA (gadolinium complex of the 1,4,7,10-tetraazacyclododecan-1,4,7,10-tetraacetic acid, N-methylglucamine salt, marketed as DOTAREM®), and Gd-HPDO3A (gadolinium complex of the 10-(2-hydroxypropyl)-1,4,7,10-tetraazacyclododecan-1,4,7-triacetic acid, marketed as ProHance®). Besides these agents, that are designed for a wholly general use, another agent that turned out to be of particular interest being both suitable for general use, and the imaging of CNS and hepatic tissue, is GD-BOPTA.

The dimeglumine salt of the Gd-BOPTA (the gadolinium complex of the 4-carboxy-5,8,11-tris(carboxymethyl)-1-phenyl-2-oxa-5,8,11-triazatridecan-13-oic acid, having the formula provided here below, and otherwise known as gadobenate dimeglumine, the Merck Index, XIII Ed. 2001, Nr 4344), is the active ingredient of the commonly used MRI contrast agent commercially known as MultiHance®, that is a 0.5 M aqueous solution of this compound.

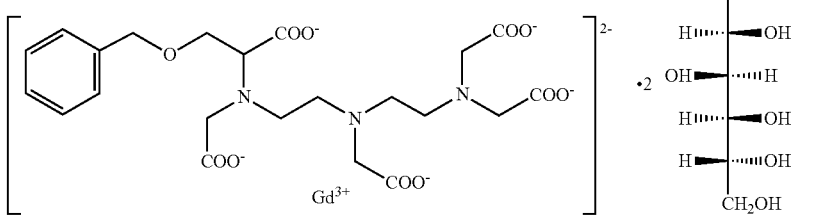

As contrast agents are commonly administered to human patients intravenously, in the form of injectable aqueous formulations, critical issues in their preparation are the purity degree with which they are isolated and their water solubility. Indeed, the quality standards fixed by International Authorities for pharmaceutical compounds are particularly stringent, especially for drugs intended for injection. Therefore, the preparation of a contrast agent in a pure, stable, and convenient physical form represents, in the most of the cases, the most challenging and crucial point that has to be addressed by any manufacturer.

To this extent, a suitable physical form should be, for instance, the one allowing a reliable and practical recovering of the intended compound in the final form, ready for use in in vivo applications, without need of further purification or formulation steps, and which can also be safely stored for prolonged times. However, whenever possible, a water soluble solid form of the chemical product, which is most easily purified and stored, is generally preferred.

The preparation of the active ingredient of MultiHance® has been described e.g. in EP0230893 and EP2503990. In more details, the gadobenate dimeglumine complex is obtained in an aqueous solution by reaction of the ligand BOPTA with a gadolinium salt, e.g. halide or acetate, or with the metal oxide Gd$_2$O$_3$, in the presence of N-methyl-D-glucamine (otherwise known as meglumine).

Attempts to isolate this contrast agent as a filterable powder by means of traditional techniques such as crystallization, solvent evaporation or lyophilisation have not been successful leading, rather, to the formation of oily products gummy, or sticky, or glassy solids that, besides being unsuitable for an industrial use, often lack the necessary water solubility.

A known process to get this MRI contrast agent in a water soluble solid form is one making use of the spray-drying technique as disclosed in EP2503990. The solid gadobenate dimeglumine collected by spray-drying displays a good water solubility and wettability and, in general, good handling properties such as, for instance, good flowability, stability, low hygroscopicity and low electrostaticity.

In a comparative example disclosed in EP2503990 (reproduced in Example 12 of the experimental section herein), an unsuccessful attempt to isolate the compound by precipitation is described, namely by adding an aqueous solution of gadobenate dimeglumine (43% w/w) to propanol solvent.

Crystallization techniques by using "antisolvents" are described, for instance, by Tung, H.; Paul, L. E.; Midler, M.; Mc Cauley, J. A.; *Crystallization of organic compounds*, Chapter 9, John Wiley & Sons, 2009.

SUMMARY OF THE INVENTION

We have now unexpectedly found that gadobenate dimeglumine can be obtained in a solid and conveniently filterable physical form by the use of appropriate dissolution and precipitation solvents and operative conditions.

In particular we have observed that when a solution of gadobenate dimeglumine in a highly polar solvent is added to an organic solvent, acting as an antisolvent, the formation of solid particles of the complex is observed, that can be filtered and dried to obtain the gadobenate dimeglumine compound in the desired solid form with high yields and in a reliable way.

Accordingly, present invention generally relates to a process for the preparation of a solid form of the gadobenate dimeglumine compound that, essentially, comprises:
  a) obtaining a solution of said compound in a suitable solvent A,
  b) adding the obtained solution to an organic solvent B acting as an antisolvent, thus inducing the formation of a solid form of the concerned gadobenate dimeglumine compound which precipitates,
  c) collecting the obtained solid precipitate.

According to another aspect, the invention relates to the gadobenate dimeglumine in the solid form obtained with the precipitation process of the present invention. The solid form of the gadobenate dimeglumine collected with the process of the invention is a filterable, water soluble, white powder having an average particle size comprised from about 1 µm to about 300 µm, even more preferably from about 5 to 100 µm.

The process of the present invention leads to the isolation of the gadobenate compound that, advantageously, complies with the quality standards fixed by International Authorities for pharmaceutical compounds.

In addition, advantageously, the solid form of the Gd-BOPTA-Dimeglumine isolated with the process of the present invention is optimally water soluble and, once collected, can conveniently be stored ready for use in the preparation of the MultiHance® formulation by simple dissolution of the collected solid compound in the proper amount of a pharmaceutically acceptable aqueous solution, including, for instance, sterile water for injections (WFI), thereby consenting a convenient simplification of the manufacturing step of the marketed formulation.

DETAILED DESCRIPTION OF THE INVENTION

Suitable solvents A for the use of the invention, namely for preparing a solution of the gadobenate dimeglumine according to the step a) of the proposed process, include highly polar solvents, preferably selected from water, aqueous solvents including saline solutions, highly polar organic solvents, and suitable mixtures thereof. In this regard, the role assumed by the amount of water, or aqueous solvent, which may be present in the solution of gadobenate dimeglumine is particularly relevant. Indeed, water-containing solutions of gadobenate dimeglumine according to the invention, namely allowing precipitation of a solid form of the complex compound, include an amount by weight of the gadobenate compound at least equal to or, preferably, exceeding the amount (by weight) of the water optionally present in the solution. In other words, the amount by weight of water optionally present in the solution is at most equal to or, preferably, is lower than the amount by weight of the gadobenate dimeglumine in solution.

On the other side, appropriate antisolvents according to the present invention, herein identified as antisolvents B or as solvent B acting as antisolvent, are, for instance, selected from organic solvents of moderate polarity that are miscible with the corresponding solvents A.

To this extent, and unless otherwise provided, with the expression "antisolvent" (or precipitation solvent, or co-solvent, as herein used interchangeably) as used herein in particular with reference to the solvent B, otherwise identified as "solvent B acting as antisolvent" or "antisolvent B", we refer to a liquid or solvent miscible with the solvent (or solvent mixture) A in which the gadobenate dimeglumine is suitably solubilized, that acts by decreasing the solubility of this compound in the resulting mixture, (i.e. the mixture obtained by addition of the solution of the gadobenate dimeglumine in the solvent A to the solvent B), thus inducing the formation of a solid precipitate of this same compound that can be isolated by filtration (see for instance, formerly cited Tung, H.; Paul, L. E.; Midler, M.; Mc Cauley, J. A. *Crystallization of organic compounds*, John Wiley & Sons, 2009).

Thus, on the one side antisolvent B shall be capable of being admixed (essentially without phase separation) with solvent A while, on the other side, it shall be able, once admixed with the solution of gadobenate dimeglumine in a solvent A, to promote a substantially quantitative precipitation of gadobenate dimeglumine as a filterable solid, preferably higher than 70%, more preferably than 80% and, most preferably, greater than 90% of the of the gadobenate in solution.

Appropriate selection of organic solvents A and antisolvents B for the use of the present invention may be based on their octanol-water partition coefficient (or partition constant or partition ratio, as alternatively used in the relevant art and herein used interchangeably), typically expressed as log P.

Octanol-water partition coefficient P is a well-known parameter which is widely used in the relevant chemical field for instance for estimating how hydrophilic or hydrophobic a chemical substance is. The value of the octanol/water partition coefficient, expressed as log P, of a wide number of organic substances, including the majority of the commonly used organic solvents has already been determined, and tables with measured log P values are, for instance, available from common Handbooks of Chemistry and Physics. (For more details on the partition coefficient P, its meaning and its determination, as well as tables listing octanol-water partition coefficients of a wide number of organic compounds, including organic solvents see, for instance, the CRC Handbook of Chemistry and Physic, 82 Edition, 2001-2002, from page 16-43 to 16-47, and the cited literature).

Organic solvents A for the use of the present invention may be selected among those having a log P value equal to, or less than, −0.5, more preferably ranging from −1.5 to −0.50 and, most preferably, from about −1.10 to −0.5, or suitable mixtures thereof.

Non-limiting examples of these solvents include, for instance, methanol (log P=−0.74), DMAC (log P=−0.77), DMF (log P=−1.01), DMSO (log P=−1,35), glycols such as, for instance, ethylene glycol (log P=−1.36) and diethylene glycol (log P=−1.47) and suitable mixtures or aqueous mixtures thereof. Among them, particularly preferred for the use of the invention is the methanol, or aqueous mixtures thereof. (With reference to log P values listed above, or elsewhere in the description see, for instance, the octanol/water partition coefficient tables provided by formerly cited CRC Handbook or provided by the US National library of Medicine, for instance available at the web site http://chem.sis.nlm.nih.gov/chemidplus).

Appropriate antisolvents B for the use of the present invention include organic solvents miscible with the elected solvent A, typically having a log P value higher than −0.5, preferably comprised from −0.5 to about 2.0, more preferably, from −0.5 to 1.5 and, most preferably, from −0.5 to 1.0. In particular, when the elected solvent A for the use of the invention is an aqueous solvent, antisolvents B are preferably selected from those having lower log P values, for instance ranging from −0.5 to 1.0, and, preferably, from −0.5 to 0.5.

On the other side, when solvent A is an organic solvent, or a mixture thereof as above said (including with water), appropriate antisolvent B for the use of the invention is preferably selected from those having log P values exceeding that of the used organic solvent A (or that of the solvent in the mixture having higher log P) of at least 0.25 and, preferably, of at least 0.5. A difference between the two log P values not higher than about 3.5 is, however, preferred, in order not to jeopardize the solvent and antisolvent miscibility required by the process of the present invention. In other words, when both the solvent A and the antisolvent B according to the invention comprise organic solvents, the difference (or delta, as herein used interchangeably) between the respective log P values (in case of mixtures, the highest for solvent A mixture and the lowest value for solvent B mixture) is a number ranging, for instance, from 0.25 to about 3.5, preferably from 0.5 to 3 and, more preferably, from 0.5 to 2.

From all the foregoing, non-limiting examples of antisolvents B according to the invention include, for instance, ketones such as acetone (log P=−0.24), methyl isobutyl ketone (MIBK) (log P=0.56), 2-butanone (log P=0.29) and cyclohexanone (log P=0.81); $C_2$-$C_5$ alcohols such as 2-propanol (log P=0.05), 2-butanol (log P=0.65), ethanol (log P=−0.30), n-butanol (log P=0.84), 2-methyl-1-propanol (log P=0.76), 1-methoxy-2-propanol (log P=−0.437) and t-butyl alcohol (log P=0.35); ether such as diethylether (log P=0.89), methyl t-butylether (log P=0.94), diethylene glycol dimethyl ether (diglyme) (log P=−0.36), tetrahydrofurane (THF) (log P=0.46) and 2-MeTHF (log P=1.85); esters such as ethyl acetate (EtAcO) (log P=0.73), as well as organic solvents such as acetonitrile (log P=−0.34) and nitromethane (log P=−0.33).

Preferred, among them, are MIBK, ethyl acetate, 2-butanol, diglyme, acetone and 2-propanol, the last two being especially preferred when the starting solution of the gadobenate dimeglumine is obtained in an aqueous solvent A.

Table 1 in the Experimental Section comprises some representative, not limiting examples of organic solvents A (vertical column, on the left side of the table) and antisolvents B (top row in the table) according to the invention and corresponding log P values. At the intersection (between solvent line and antisolvent column) the table shows the value of the delta between the two log P values calculated for the concerned pair of organic solvent A: antisolvent B.

An object of the present invention, therefore, concerns a process for the preparation of a solid form of the gadobenate dimeglumine compound of the above formula (II) that comprises the main steps of:

a) obtaining a solution of the gadobenate dimeglumine in a solvent A selected from water, aqueous solvents, organic solvents having a log P value equal to or less than −0.5 and suitable mixtures or aqueous mixture thereof, wherein the amount by weight of the water optionally present in the solution is at most equal to or lower than the amount by weight of the gadobenate compound comprised in the solution;

b) adding the obtained solution to an appropriate organic solvent B acting as antisolvent, to achieve the formation of a solid form of the gadobenate dimeglumine;

c) collecting the obtained solid form of the gadobenate dimeglumine.

According to the proposed process, a solution of the gadobenate dimeglumine compound is first obtained in a solvent A, as above set forth.

To this extent, the concentration of the gadobenate in the obtained solution can suitably vary from 1% to an upper limit determined based on the gadobenate dimeglumine solubility in the elected solvent, or solvents mixture, and reaching a value up to about 70%, for instance when the solvent A is water or an aqueous solvent such as, for instance, a saline solution, in which the gadobenate compound has a higher solubility. Higher concentrations (of the gadobenate compound in the solvent A), for instance of at least 10% or, preferably, equal to or higher than 20%, are, however, preferred for the use of the invention, conveniently reducing organic solvent waste.

To this extent, the starting solution of the gadobenate dimeglumine compound in the solvent A can be suitably obtained at a temperature lower than 100° C. and, for instance, comprised from 20° C. to 100° C., wherein the use of higher temperature, for instance preferably comprised from 35° C. up to about 85° C., allows for more concentrated starting solutions.

According to one preferred embodiment, the process of the invention comprises obtaining a suitable solution of the gadobenate dimeglumine in water or an aqueous solvent A. To this extent, and as formerly discussed, the concentration of said solution is at least 50% w/w, that is to say a solution where the amount by weight of the gadobenate compound is at least equal to that of the water in the solution, thereby counteracting the high solubility and hygroscopicity of this compound in an aqueous medium, which might affect the precipitation of the solid form of the complex compound.

More particularly, according to one practical implementation, the step a) of the process of the invention comprises obtaining an aqueous solution of the gadobenate dimeglumine by reacting the chelating ligand BOPTA with gadolinium oxide ($Gd_2O_3$), in water and in the presence of meglumine, at a reaction temperature for instance from 40° C. to 100° C. and, preferably, of about 80° C., and then, optionally, suitably concentrating the obtained solution. Alternatively, the aqueous solution of the gadobenate dimeglumine first obtained according to the step a) of the proposed process is derived from the industrial process for the preparation of this complex compound. To this extent, the concentration of said industrially obtained gadobenate dimeglumine solution is then adjusted at a desired value, preferably by partial evaporation of water, which can be performed according to conventional methods, up to a final concentration of at least 50% w/w, as said, preferably ranging from 53% to 65% and, more preferably, from 60% to 65% w/w.

According to an alternative embodiment, the step a) of the process of the invention comprises obtaining a solution of the gadobenate dimeglumine in an organic solvent A.

To this extent, the aqueous solution of the gadobenate dimeglumine, for instance obtained from the industrial process for the preparation of the gadobenate dimeglumine complex compound, is treated to remove the water solvent, typically by concentration under vacuum or distillation, to a final concentration for instance higher than 65% (w/w) and up to an oily residue, or, alternatively, by lyophilization of the industrial solution, and the obtained residue is then diluted, or solubilized, depending on the case, with the appropriate amount of an organic solvent A leading to an organic solution of the gadobenate dimeglumine of the desired concentration. Said concentration is at least about 5% w/w and, preferably, higher than 10%, more preferably higher than 15%, and most preferably higher than 20% up to an upper limit which depends on the solubility of the gadobenate dimeglumine in the elected solvent A, and reaching, for instance, a value of about 50% (w/w) in preferred organic solvents where the gadobenate shows an increased solubility.

For example, when methanol is used as the solvent A, according to one of the preferred embodiments of the instant invention, a starting solution of the gadobenate compound is obtained in this solvent with a concentration ranging from 25% to about 50% and, more preferably, 35% to about 50%, being the above upper limit consistent with the solubility of the gadobenate complex in this solvent. When, instead, organic solvents A are used in which the gadobenate dimeglumine is less soluble, as is the case, for instance, of DMF, then less concentrated gadobenate solutions, e.g. ranging from about 5% to about 15% (w/w), can also be used profitably, without incurring in unwanted reductions of the precipitation yield.

The organic solution of the gadobenate compound obtained according to the step a) of the process of the invention may, optionally, include an amount of water, for instance an aqueous solvent residue. To this extent, the amount (by weight) of water or residual aqueous solvent in the organic solution is herein conveniently expressed by reference to the amount (by weight) of gadobenate in solution, as per cent of the amount by weight of the gadobenate dimeglumine compound, according to the following equation $$\% \text{ water amount} = 100 \times \frac{\text{amount of water (g)}}{\text{amount of gadobenate dimeglumine (g)}}$$

According to the foregoing, the amount of water in the organic solution according to the invention is less than about 55% and, preferably less than 35% of the amount by weight of the gadobenate dimeglumine in solution; more preferably the water amount in solution is from 5% to 20% and, particularly preferably, from 8% to 15% of the amount by weight of the gadobenate complex in solution.

In a still alternative embodiment of the invention, the step a) of the process comprises obtaining a suitable starting solution of the gadobenate dimeglumine by solubilization of solid gadobenate compound, for instance recovered by a spray drying procedure, or, alternatively, by lyophilization of an aqueous solution of the product, in the proper amount of the selected solvent A leading to a gadobenate solution of the desired concentration.

Once prepared, the collected solution of the gadobenate dimeglumine in the solvent A is added to the appropriate antisolvent B.

In particular, according to the step b) of the process of the present invention, the solution of the gadobenate dimeglumine deriving from step a) is slowly added to a suitable antisolvent B maintained, for all the time of the addition, under appropriate stirring and temperature conditions, thus causing the progressive precipitation of a filterable solid form of the said concerned contrast agent.

In this regard, the amount by weight of antisolvent B that is used according to the process of the invention preferably exceeds that of the gadobenate dimeglumine compound within the solution (of this contrast agent) deriving from the step a) of the process. In particular, the amount by weight of the antisolvent B is preferably at least 4 times higher, for example from 4 to 100 times, preferably from 4 to 50 and, more preferably, from 4 to 20 times the amount (by weight) of the gadobenate dimeglumine in solution.

According to the process of the present invention, the addition of the gadobenate solution to the appropriate antisolvent is preferably performed gradually over the time, for instance in portion or, preferably, dropwise, or with a constant flow rate, by operating according to conventional means, in a time taking up to 10 hours, preferably from 1 to 8 hours, and, more preferably, ranging from 2 to 6 hours. Throughout the said addition period, the antisolvent B is properly maintained under vigorous stirring and at a suitable temperature, for instance below 50° C.

More particularly, according to a preferred embodiment, the step b) of the process of the present invention comprises adding, over an appropriate period of time, as detailed above, the solution of the gadobenate dimeglumine (in the solvent A) to the appropriate antisolvent B. Antisolvent B is preferably kept (for the entire time of the addition) under vigorous stirring. The addition mixture (including the antisolvent B and the added solution of the gadobenate dimeglumine) is also preferably kept at a controlled temperature ranging, for instance, from 0 to 50° C., preferably from 0 to 25° C., more preferably from 0 to 10° C. and, even more preferably, from 0 to 5° C., though temperatures below 0° C., e.g. preferably comprised from 0 and −10° C., can profitably be used when the solvent A is an organic solvent.

The expression "vigorous stirring as used herein, and unless otherwise indicated, comprises a stirring of at least 200 rpm (revolutions per minute) and, preferably, from 250 to 450 rpm, when operating on a pre-industrial or pilot scale, or a corresponding vigorous stirring obtainable with industrial equipment, when operating on an industrial scale.

In practical terms, according to one preferred practical implementation of the proposed process, a starting aqueous solution of the gadobenate compound, for instance obtained by suitable concentration of the aqueous solution from the industrial process for the preparation of the gadobenate dimeglumine complex compound, is added over a time period of at least about 4 hours and, preferably, of from 4 to 8 hours, to an appropriate antisolvent suitably stirred and cooled (for the whole addition time) at a temperature from 0 to 10° C. and, preferably, from 0 to 5° C.

When, instead, a solution of the gadobenate dimeglumine is obtained in an organic solvent A, according to a particularly preferred embodiment of the process of the invention, the almost quantitative precipitation of solid gadobenate is advantageously obtained over a period of time ranging, preferably, from 2 to 6 hours, and, more preferably, in less than 4 hours, considering the time of addition of the gadobenate solution in the antisolvent B kept, the latter, under stirring at temperatures close to or lower than room temperature, for example ranging from 10° C. to 25° C.

From all the foregoing, by applying the operating conditions set forth by the process of the present invention, the progressive precipitation of the solid form of the gadobenate dimeglumine is obtained, that can thus be collected by filtration, according to the step c) of the process of the invention.

To this extent, for instance, the obtained solid gadobenate can be suitably collected immediately, i.e. at the end of the addition, or, alternatively, the precipitate can be maintained under stirring, for instance for a few hours, at the same or even lower temperature, for example from 0 to 10° C., as described in better details in the experiment section below, and then filtered to give the desired solid form of the contrast agent with good yield and in a reliable way.

More particularly, the step c) of the process of the invention comprises collecting, by filtration, the gadobenate dimeglumine in solid form obtained by precipitation at the step b) of the process; the collected precipitate is preferably washed with antisolvent B and then dried, for instance under reduced pressure, to obtain a white solid powdery residue.

Alternatively, the wet filtrate can be properly washed, or further washed, with a more volatile solvent, typically a low boiling solvent such as acetone or a suitable ether, as better detailed in the experimental section that follows, thereby obtaining by filtration and appropriate drying step a solid form of the gadobenate dimeglumine with a minimized amount of residual water or organic solvent.

According to one embodiment of the invention, the step c) of the instant process is carried out under normal air conditions or, according to an alternative embodiment, it may be suitably carried out under an inert atmosphere.

To this extent, working conditions using an inert atmosphere are particularly preferred when the solvent A is water or an aqueous solvent such as, for instance, the one in which is dissolved the gadobenate dimeglumine directly obtained by the industrial process for the preparation of the Gd-BOPTA complex compound. In this case, in fact, a hygroscopic wet solid may be obtained, which is preferably filtered, washed and dried under an inert atmosphere, typically under nitrogen or argon atmosphere.

From all the foregoing, the process of the present invention allows to conveniently isolate and collect the meglumine salt of the gadobenate complex with high yields and in a substantially pure solid form, i.e. with negligible amounts of side products or unreacted materials, such as the free chelating agent, or the free metal.

Advantageously, moreover, the process of the present invention allows to recover gadobenate dimeglumine in a workable, water-soluble solid form, suitable for the preparation of pharmaceutical injectable compositions of the gadobenate complex compound, from substantially any production batch of the product. For instance, gadobenate meglumine may be recovered from production batches which may be obtained, for accidental reasons or technical or procedural problems, in a undesirable glassy or rubbery form, or, in any case, in a form which is not highly soluble in water, and thus unsuitable for the preparation of the injectable contrast agent composition.

To this extent, Examples 11, 12 and 13 of the Experimental Section below show that a water-soluble and suitably workable solid form of the GD-BOPTA-dimeglumine can conveniently be recovered by using the process of the invention from a gummy solid recovered according to the comparative example 2C of EP2503990, or a glassy or unworkable solid form of the complex, for instance formed during an altered preparation of the contrast agent.

Therefore, in a further embodiment, the present invention relates to a process for the recovery of gadobenate dimeglumine in a water soluble and suitably workable solid form, that comprises obtaining a solution of the gadobenate dimeglumine according to the step a) of the process by solubilizing a water insoluble or hardly workable form of said complex compound in a suitable solvent A.

The invention further relates to the solid form of the gadobenate dimeglumine directly obtained by the process of the invention, as widely described above.

To this extent, the solid form of the gadobenate dimeglumine obtained according to the invention is a stable, water soluble powdered solid having a particle size from 1 µm to 300 µm, and preferably comprised from 5 µm to 100 µm.

As formerly discussed, the complex compound collected with the proposed process is endowed with a good stability, favorable workability and, especially, optimal water solubility. Indeed, it has proven to possess optimal water-dissolution characteristics, requiring less than 1 mL of water for 1 g of product at 25-30° C., to have complete ready dissolution in less than five minutes.

Moreover, after its isolation, the collected solid product can conveniently be stored for long periods of time, for instance up to 2 years when properly stored, (i.e. under inert atmosphere) in a form that is ready for use in the preparation of the MultiHance® formulation, by simple dissolution of the solid compound in the proper amount of a pharmaceutically acceptable aqueous solution, such as, for instance, the sterile water for injections (WFI) or any another proper aqueous medium, according to procedures commonly employed in the art.

For instance, the solid form of the Gadobenate Dimeglumine collected at the step c) of the process may be stored and transported without need of specific temperature control and in particular it may be supplied to hospitals and physicians for on-site formulation into a ready-to-use administrable solution without requiring such users to have special storage facilities.

Preferably, in such a case it can be supplied in the form of a two-component kit, which can include two separate containers or a dual-chamber container. In the former case a first container contains the solid form of the Gadobenate and the second container contains a physiologically acceptable carrier. Examples of suitable carriers include, for instance, water, typically sterile, pyrogens free water (which may also be indicated as water for injection), aqueous solution such as saline solution (which may advantageously be balanced so that the final product for injections is not hypotonic), or aqueous solutions of one or more tonicity adjusting substances such as salts or sugars, sugar alcohol, glycols or other non-ionic polyol materials (e.g. glucose, sucrose, glycerol, glycols and the like).

Preferably the container is a conventional septum-sealed vial, wherein the vial containing the solid product of step c) is sealed with a septum through which the carrier liquid stored in the second container may be injected using an optionally prefilled syringe. In such a case, a syringe may be used as the convenient container of the second component is also used then for injecting the contrast agent.

In the latter case, preferably the dual-chamber container is a dual-chamber syringe and once the solid form of the Gadobenate dimeglumine has been reconstituted and then suitably mixed or gently shaken, the container can be used directly for injecting the contrast agent.

Therefore, besides providing for a solid pure product in a reliable way, with good yields, the process of the invention allows to conveniently simplify and fully standardize the preparation of MultiHance® marketed formulation.

Interestingly, moreover, the proposed process allows to achieve all these results using conventional, multipurpose equipment, i.e. without requiring specifically devoted instruments or technology, such as, for instance, a spray-dryer, thereby making the process of the present invention advantageously flexible and versatile.

From all the above, it will be apparent that the process of the present invention, comprising obtaining a suitable solution of the said compound in a solvent A, adding, under stirring and appropriate temperature conditions, said obtained solution in a suitable organic antisolvent B, thus inducing the precipitation of solid particles of the complex compound that are collected by filtration, washed and dried under reduced pressure and, optionally, under inert atmosphere, enables the isolation of a water soluble solid form of the gadobenate dimeglumine which can conveniently be stored, or packaged as a kit of parts, ready for use in the simplified and reliable preparation of the MultiHance® marketed formulation.

Noteworthy, the process of the invention may be conveniently employed even on a large scale, for the preparation of a gadobenate dimeglumine compound intended for the use as diagnostic agents.

The following examples of the practice of the present invention are meant to support the consistency and reliability of the process of the present invention. However, it should be understood that the particular embodiments illustrating the present invention are meant to be illustrative and are in no way limiting the scope of the invention.

Experimental Part

EXAMPLE 1

Preparation of an Aqueous Solution of Gadobenate Dimeglumine

A solution of BOPTA (209.7 g; assay 92%, 0.375 mol) and N-methyl-D-glutamine (meglumine) (146.4 g; 0.750 mol) in water (240 mL) was added to a suspension of gadolinium oxide (68.85 g; 0.190 mol) in water (210 mL) and the mixture was kept under stirring at 80° C. for about 75 min.

The mixture was then cooled to room temperature and filtered, and its pH was adjusted to 6.9-7.0 by addition of meglumine. The obtained solution (concentration: 0.53 mol/L, corresponding to about 46% (w/w)) that is adjusted to the desired value, for instance by concentration under vacuum.

EXAMPLE 2

Preparation of Solid Gadobenate Dimeglumine by Use of an Aqueous Solvent and 2-propanol, Respectively as Solvent A and Antisolvent B In a 3 L reactor, equipped with a mechanical stirrer, 2-propanol (1858 g) was added and cooled to 2° C. An aqueous solution of gadobenate dimeglumine obtained as in the example 1, then further concentrated (310.2 g, 62.7% w/w, corresponding to an amount by weight of water of 59.5%, calculated as percent ratio versus the amount by weight of gadobenate in the solution) and maintained at room temperature, was added dropwise in 6 h to 2-propanol, kept under strong stirring (300 rpm). The obtained slurry was stirred at 2° C. for further 16 h. Then it was filtered in an inert atmosphere and the collected solid was washed with 2-propanol (450 mL).

The wet solid was dried for 5 h at 30 mbar 30° C., obtaining a white powder (193.8 g; yield 93.4%, calculated on anhydrous and solvent free basis; loss on drying 6.3%; water content 3.0%).

EXAMPLE 3

Preparation of Solid Gadobenate Dimeglumine by Use of an Aqueous Solvent and Acetone, Respectively as Solvent A and Antisolvent B In a 3 L reactor, equipped with a mechanical stirrer, acetone (1700 g) was added and cooled to 2° C. Then an aqueous solution of gadobenate dimeglumine (180.0 g; 62.7% w/w), kept at room temperature, was added dropwise in 6 h, keeping the 3 L reactor under strong stirring (300 rpm). The mixture was stirred at 2° C. for further 16 h. Then it was filtered in an inert atmosphere and washed with acetone (700 mL).

The wet solid was dried for 5 h at 30 mbar 30° C., obtaining a white powder (108.6 g; yield 90,1%, calculated on anhydrous and solvent free basis; loss on drying 6.4%; water content 3.91%).

EXAMPLE 4

Preparation of Solid Gadobenate Dimeglumine by Use of MeOH and 2-propanol, Respectively as Solvent A and Antisolvent B A gadobenate dimeglumine solution (0.5 M; 350 mL), prepared according to the procedure described example 1, was concentrated under reduced pressure (50-70 mbar; 50° C.) to oily residue. The residue was dissolved in 170 g of MeOH at 40° C. (concentration of the obtained gadobenate dimeglumine solution: approximately 48%, water content 14%, calculated as percent ratio versus the amount by weight of gadobenate in the solution). After cooling to room temperature the obtained solution was added in 5 h to a 3 L reactor containing 2-propanol (1500 g), previously cooled to 2° C.; during the addition the reactor was kept under stirring (250 rpm). The mixture was stirred at 2° C. for further 16 h and then was filtered in nitrogen atmosphere; the wet solid was washed with 2-propanol (500 mL).

The wet solid was dried for 5 h at 35 mbar and 30° C., and for 4 h at 8 mbar 40° C., obtaining a white powder (183.2 g; yield 95.4%, calculated on anhydrous and solvent free basis; loss on drying 3.60%).

EXAMPLE 5

Preparation of Solid Gadobenate Dimeglumine by Use of MeOH and Acetone, Respectively as Solvent A and Antisolvent B A gadobenate dimeglumine solution (0.5 M; 186.5 mL), prepared according to the procedure described example 1, was concentrated under reduced pressure (50-70 mbar; 50° C.) to oily residue. The residue was dissolved in 140 g of MeOH at 40° C. (concentration of the gadobenate dimeglumine solution approximately 47%, water content 11%, calculated as percent ratio versus the amount by weight of gadobenate in the solution). After cooling to room temperature the obtained solution was added (addition time: 4 h) to a 1.5 L reactor containing acetone (800 g) kept at 25° C. and under stirring for the whole time of addition. The mixture was stirred at 25° C. for further 1 h, then was filtered and the wet solid was washed with acetone (500 mL).

The wet solid was dried for 16 h at 35 mbar 40° C., obtaining a white powder (109.1 g; yield 98.1% calculated on anhydrous and solvent free basis; loss on drying 11.3%).

The solid was further dried at 60° C. and 10 mbar for another 40 h to reach a loss on drying of 4.6%

EXAMPLE 6

Preparation of Solid Gadobenate Dimeglumine by Use of MeOH and Ethyl Acetate, Respectively as Solvent A and Antisolvent B A 1.5 L reactor, equipped with a mechanical stirrer, was loaded with ethyl acetate (800 g) and cooled to 5° C. Then a gadobenate dimeglumine solution in methanol (220 g; 45% w/w; water content 3.52%, calculated as percent ratio versus the amount by weight of gadobenate in the solution), kept at room temperature, was added, dropwise, in the cooled acetate, in a time of about 6 h. The obtained mixture was stirred at 5° C. for 1 additional hour, then filtered and washed with ethyl acetate (400 mL).

The collected wet solid was dried for 16 h at 25 mbar 40° C., obtaining a white powder (103.4 g; quantitative yield, calculated on anhydrous and solvent free basis; loss on drying 3.83%).

EXAMPLE 7

Preparation of Solid Gadobenate Dimeglumine by Use of MeOH and Dyglime, Respectively as Solvent A and Antisolvent B In a 2 L reactor, equipped with a mechanical stirrer, diglyme (800 g) was added and cooled to 10° C. Then gadobenate dimeglumine solution in methanol (285 g; 35% w/w; water content 3.42%, calculated as percent ratio versus the amount by weight of gadobenate in the solution), kept at room temperature, was added in 3 h, keeping the reactor under strong stirring. The mixture was stirred at 10° C. for further 2 h, then the solid was filtered, washed with diglyme (300 mL) and dried for 16 h at 25 mbar 40° C., and for another 25 h at 60° C. 5 mbar obtaining a white powder (110.9 g; yield 96.4%, calculated on anhydrous and solvent free basis; loss on drying 12.4%).

The obtained solid was then further suspended in acetone (300 g), kept under stirring for 4 h, filtered and dried for 45 h at 10 mbar 60° C. by obtaining a 96.8 g of a final solid (yield 98.1, loss on drying 1.5%; water content 0.92%).

EXAMPLE 8

Preparation of Solid Gadobenate Dimeglumine by Use of DMF and 2-propanol, Respectively as Solvent A and Antisolvent B A gadobenate dimeglumine solution (0.5 M; 150 mL), prepared according to the procedure described example 1, was partially concentrated under reduced pressure (90-120 mbar; 50° C.; distilled water 50 g). The residue was diluted in DMF (610 g) and the distillation was continued to remove a further amount of water (25 g). After cooling to room temperature, the obtained solution (gadobenate dimeglumine concentration 11.0%, water content 36,4% (calculated as percent ratio versus the amount by weight of gadobenate in the solution)) was added in 4 h to a 3 L reactor containing 2-propanol (1000 g), kept under stirring at 5° C. The mixture was stirred at 5° C. for further 1 h. Then it was filtered and the wet solid was washed with 2-propanol (500 mL).

The wet solid was dried for 24 h at 5 mbar 40° C., obtaining a white powder (74.3 g; yield 89.6%, calculated on anhydrous and solvent free basis; loss on drying 4.24%).

EXAMPLE 9

Preparation of Solid Gadobenate Dimeglumine by Use of an Aqueous Solution of Gadobenate Having a Concentration of 50% (w/w) and 2-propanol as Antisolvent B In a 1.5 L reactor, equipped with a mechanical stirrer, 2-propanol (850 g) was added and cooled to 2° C.

Then, maintaining the reactor under strong stirring, an aqueous solution of gadobenate dimeglumine (90.4 g, concentration 50% w/w), kept at room temperature, was added in 3 h; the obtained suspension was stirred at 2° C. for further 1.5 h.

Gadobenate dimeglumine initially precipitated as a thin solid but, at the end of the addition, the precipitate started to become sticky, forming progressively crusts and lumps.

The preparation was repeated in the same conditions, with the only difference that, just finished the addition, the slurry was filtered immediately, by operating under nitrogen. A slightly sticky solid was thus obtained, that was washed with acetone (100 g) and dried at 35° C. 20 mbar for 16 h, obtaining a white coarse powder (31.6 g; yield 69.0%, calculated on anhydrous and solvent free basis; loss on drying 1.2%; water content 0.7%).

EXAMPLE 10

Preparation of Solid Gadobenate Dimeglumine by Use of an Aqueous Solution of Gadobenate with a Concentration 53% (w/w) and 2-propanol as Antisolvent B In a 1.5 L reactor, equipped with a mechanical stirrer, 2-propanol (850 g) was added and cooled to 2° C. Then, maintaining the reactor under strong stirring, an aqueous solution of gadobenate dimeglumine, prepared as described in example 1 and further concentrated (102 g; concentration 53.3% w/w), kept at room temperature, was added in 2.5 h.

The mixture was stirred at 2° C. for further 1 h. The solid was filtered and dried at 30° C. 30 mbar for 17 h (40.7 g; yield 70.9%, calculated on anhydrous and solvent free basis; loss on drying 5.2%; water content 1.83%).

EXAMPLE 11

Recovery of Water Soluble Gadobenate Dimeglumine from a Glassy, Water Insoluble form of the Complex by Using MeOH and 2-butanol, Respectively as Solvent A and Antisolvent B A gadobenate dimeglumine solution (0.5 M; 172 mL), prepared according to the procedure described example 1, was lyophilized. A glassy solid was obtained that was then dissolved with 122 g of MeOH at 45° C. (gadobenate dimeglumine concentration 40% w/w; water content 14.6% (calculated as percent ratio versus the amount by weight of gadobenate in the solution)). The obtained solution was cooled to 20° C. and then added, in about 3 h, into 1 L reactor loaded with 2-butanol (726 g) cooled at 10-15° C. and kept under stirring. The mixture was then stirred at 15° C. for one additional hour, then was filtered and the wet solid was washed with acetone (250 g).

The wet solid was dried under vacuum for 18 h at 40° C., and for 5 h at 60° C. obtaining a white powder (84.3 g; yield 94.4% calculated on anhydrous and solvent free basis; loss on drying 1.90%)

EXAMPLE 12

Recovery of Water Soluble Gadobenate Dimeglumine from a Unworkable Form of the Complex Compound by Using MeOH and Acetone, Respectively as Solvent A and Antisolvent B Operating according to the conditions reported in EP2503990 comparative example 2C, a gadobenate dimeglumine solution (0.5 M; 100 mL, about 43% w/w) was dropwise added to a reactor containing 2-propanol (2 L) stirred at room temperature; a sticky gummy solid, forming lumps and crusts on the reactor stirrer and walls, was obtained. The solvent was removed by decantation and the solid was dissolved in MeOH (130 g) at 45° C. The obtained solution was concentrated under reduced pressure (70-90 mbar; 35° C.) to obtain a final weight of 130.8 g (gadobenate dimeglumine concentration 40.4% w/w; water content 10.1% (calculated as percent ratio versus the amount by weight of gadobenate in the solution).

The obtained solution was cooled to 25° C. and then added, in 2 h, to a reactor containing acetone (450 g) kept, during all the addition time, at 19° C. and under vigorous stirring. The mixture was kept at 19° C. and under stirring for additional 4 h, then was filtered and the wet solid was washed with acetone (150 g).

The wet solid was dried under vacuum for 17 h at 40° C., and for 43 h at 60° C. (43.9 g; yield 86.9% calculated on anhydrous and solvent free basis; loss on drying 4.6%).

EXAMPLE 13

Recovery of Water Soluble Gadobenate Dimeglumine from a Water-Insoluble Form of the Complex Compound by Using Ethylene Glycol and 2-propanol, Respectively as Solvent A and Antisolvent B and Washing the Collected Wet Solid with Diisopropyl Ether A gadobenate dimeglumine solution (0.5 M; 66.3 mL), prepared according to the procedure described example 1, was lyophilized. A glassy solid was obtained that was successively dissolved at 45° C. with 61.4 g of ethylene glycol, obtaining 100 g of a gadobenate dimeglumine solution with concentration of 35.1% w/w and a residual water content of 10.1% (calculated as percent ratio versus the amount by weight of gadobenate in the solution).

In a 1 L reactor, equipped with a mechanical stirrer, 2-propanol (450 g) was added and cooled to 10° C. The solution of gadobenate dimeglumine in ethylene glycol, kept at room temperature, was then added in 1 h, keeping the reactor under strong stirring. The obtained solid precipitate was filtered and washed with diisopropyl ether (100 g); then the wet panel was re-suspended with 300 g of diisopropyl ether and kept under stirring for 2 h. The solid was filtered and dried for 17.5 h at 25 mbar 40° C. (30.76 g; yield 87%, calculated on anhydrous and solvent free basis; loss on drying 0.7%).

TABLE 1

| | | ANTISOLVENT B | | | | | | | | | | |
|---|---|---|---|---|---|---|---|---|---|---|---|---|
| Organic solvent A | Log P | Acetone −0.24 | MIBK 0.56 | 2-propanol 0.05 | 2-butanol 0.65 | Diglyme −0.36* | AcOEt 0.73 | 1-methoxy-2-propanol −0.44 | THF 0.46 | Diethyl ether 0.89 | 2-Butanone 0.29 | n-butanol 0.84 | CH$_3$CN −0.33 |
| MeOH | −0.74 | 0.5 | 1.3 | 0.79 | 1.39 | 0.38 | 1.47 | 0.30 | 1.2 | 1.63 | 1.03 | 1.58 | 0.41 |
| DMF | −1.01 | 0.77 | 1.57 | 1.06 | 1.66 | 0.65 | 1.74 | 0.57 | 1.47 | 1.9 | 1.3 | 1.85 | 0.68 |
| DMAC | −0.77 | 0.53 | 1.33 | 0.82 | 1.42 | 0.41 | 1.50 | 0.33 | 1.23 | 1.66 | 1.06 | 1.61 | 0.44 |
| DMSO | −1.35 | 1.11 | 1.91 | 1.4 | 2 | 0.99 | 2.08 | 0.91 | 1.81 | 2.24 | 1.64 | 2.19 | 1.02 |
| ETHYLENE GLYCOL | −1.36* | 1.12 | 1.92 | 1.41 | 2.01 | 1 | 2.09 | 0.92 | 1.82 | 2.25 | 1.65 | 2.20 | 1.03 |
| DIETHYLENE GLYCOL | −1.47* | 1.23 | 2.03 | 1.52 | 2.12 | 1.11 | 2.2 | 1.03 | 1.93 | 2.36 | 1.76 | 2.31 | 1.14 | log P values are from CRC Handbook of Chemistry and Physic, 82 Edition, 2001-2002, from page 16-43 to 16-47, or (labelled with *) from U.S. National Library of Medicine, by the U.S. National Institute of Health.

The invention claimed is:

1. A process for a preparation of a solid form of gadobenate dimeglumine compound of formula

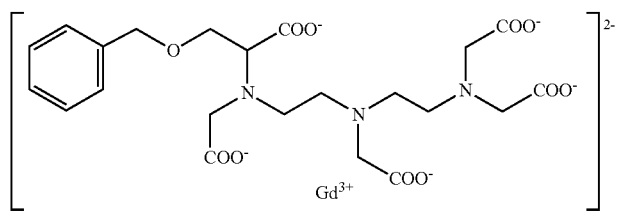 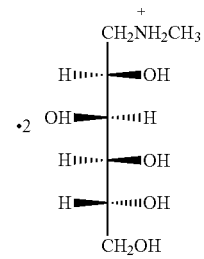

that comprises:
  a) obtaining a solution of the gadobenate dimeglumine in a solvent A selected from the group consisting of water, aqueous solvents, organic solvents having a log P value no greater than −0.5, and mixtures thereof, wherein the amount by weight of the water optionally present in the solution is no more than the amount by weight of the gadobenate dimeglumine in the solution;
  b) adding the obtained solution of the gadobenate dimeglumine to an antisolvent B, wherein the antisolvent B is maintained under stirring and at a temperature below 50° C., and wherein the amount by weight of the antisolvent B is at least 4 times the amount by weight of gadobenate dimeglumine, to obtain the solid form of the gadobenate dimeglumine; and
  c) collecting the obtained solid form of the gadobenate dimeglumine.

2. The process according to claim 1, wherein the temperature is maintained from 0 to 25° C.

3. The process according to claim 2, wherein the step a) comprises obtaining a solution of the gadobenate dimeglumine in an organic solvent A having a log P value of from −1.5 to −0.5.

4. The process according to claim 2, wherein the step a) comprises obtaining a solution of the gadobenate dimeglumine in water or an aqueous solvent A with a concentration of the gadobenate dimeglumine at least 50% w/w.

5. The process according to claim 4, wherein the concentration of the gadobenate dimeglumine in the obtained solution of the gadobenate dimeglumine is of from 53% to 65% (w/w).

6. The process according to claim 3, wherein the step a) comprises obtaining a solution of the gadobenate dimeglumine by concentrating an aqueous solution of the gadobenate dimeglumine to a concentrated solution with a concentration of the gadobenate dimeglumine from 65% (w/w) up to an oily residue, and then diluting said concentrated solution, or solubilizing said oily residue, with an amount of the organic solvent A to give the solution of the gadobenate dimeglumine.

7. The process according to claim 6, wherein the solution of the gadobenate dimeglumine comprises an amount of water or a residual aqueous solvent which, by weight, is less than 35% of the amount by weight of the gadobenate dimeglumine in solution.

8. The process according to claim 3, wherein the organic solvent A is selected from the group consisting of methanol, DMSO, DMAC, DMF, ethylene glycol, di-ethylene glycol, and mixtures thereof.

9. The process according to claim 4, wherein step b) comprises adding the obtained solution of the gadobenate dimeglumine to an antisolvent B having a log P value ranging from −0.5 to 1.0.

10. The process according to claim 9, wherein the antisolvent B is maintained under stirring at a temperature of from 0 to 10° C.

11. The process according to claim 10, wherein the addition of the solution of the gadobenate dimeglumine to the antisolvent B is performed in a time ranging from 1 to 8 hours.

12. The process according to claim 9, wherein the antisolvent B is selected from the group consisting of acetone and 2-propanol.

13. The process according to claim 6, wherein the step b) comprises adding the obtained solution of the gadobenate dimeglumine to an antisolvent B having a log P value ranging from −0.5 to about 2.0, wherein the log P value of the antisolvent B exceeds the log P value of the solvent A by a value ranging from 0.25 to about 3.5.

14. The process according to claim 13, wherein the antisolvent B is maintained under stirring and at a temperature from 10 to 25° C.

15. The process according to claim 14, wherein the addition of the solution of the gadobenate dimeglumine to the anti solvent B is performed in a time of from 2 to 6 hours.

16. The process according to claim 13, wherein the antisolvent B is selected from the group consisting of MIBK, 2-butanone, cyclohexanone, 2-propanol, 2-butanol, ethanol, n-butanol, 2-methyl-1-propanol, t-butyl alcohol, 1-methoxy-2-propanol, diethylether, methyl t-butylether, diglyme, THF, 2-MeTHF, ethyl acetate, acetonitrile, and nitromethane.

17. The process according to claim 9, wherein the amount by weight of the anti solvent B is from 4 to 100 times the amount by weight of the gadobenate dimeglumine.

18. The process according to claim 9, wherein step c) comprises collecting by filtration, optionally carried out under an inert atmosphere, the solid form of the gadobenate dimeglumine obtained at the step b) of the process to obtain a filtrate, optionally washing the filtrate with a low-boiling solvent, and drying it.

19. The process according to claim 1, wherein the pair of the solvent A:the antisolvent B is selected from the group consisting of: water:2-propanol; aqueous solvent:acetone; MeOH:2-propanol; MeOH:acetone; MeOH:AcOEt; MeOH:

Diglyme; DMF:2-propanol; MeOH:2-butanol; ethylene glycol:2-propanol; MeOH:n-butanol; and MeOH:MIBK.

20. The process according to claim 1, wherein the step a) of the process comprises obtaining a solution of the gadobenate dimeglumine by solubilizing a water insoluble or glassy solid form of the gadobenate dimeglumine in a solvent A.

* * * * *